US00PP28222P3

(12) United States Plant Patent
Kobayashi

(10) Patent No.: US PP28,222 P3
(45) Date of Patent: Jul. 25, 2017

(54) POINSETTIA PLANT NAMED 'PER1360'

(50) Latin Name: ***Euphorbia pulcherrima* Willd.**
Varietal Denomination: PER1360

(71) Applicant: Ruth Kobayashi, Carlsbad, CA (US)

(72) Inventor: Ruth Kobayashi, Carlsbad, CA (US)

(73) Assignee: Dümmen Group B.V., De Lier (NL)

( * ) Notice: Subject to any disclaimer, the term of this patent is extended or adjusted under 35 U.S.C. 154(b) by 102 days.

(21) Appl. No.: 14/545,489

(22) Filed: May 12, 2015

(65) Prior Publication Data

US 2016/0338244 P1 Nov. 17, 2016

(51) Int. Cl.
*A01H 5/02* (2006.01)

(52) U.S. Cl.
USPC ..... Plt./307

(58) Field of Classification Search
USPC ..... Plt./263.1, 302, 303, 307
See application file for complete search history.

(56) References Cited

PUBLICATIONS

PLUTO: Plant Variety Database, Oct. 18, 2016, citation for PER1360. 1 page.*

* cited by examiner

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of Poinsettia plant named 'PER1360', characterized by its uniform, upright and mounded plant habit; vigorous growth habit; freely and upright branching habit; dark green-colored leaves; under natural season conditions, plants flower on or about November 10 in Southern California; large inflorescences with medium red-colored flower bracts; and good post-production longevity.

2 Drawing Sheets

Botanical designation: *Euphorbia pulcherrima* Willd.
Cultivar denomination: 'PER1360'.

BACKGROUND OF THE INVENTION

The present invention relates to a new and distinct cultivar of Poinsettia plant, botanically known as *Euphorbia pulcherrima* Willd., and hereinafter referred to by the cultivar name 'PER1360'.

The new Poinsettia plant is a product of a planned breeding program conducted by the Inventor in Encinitas, Calif. The objective of the breeding program is to create new uniform Poinsettia plants having large inflorescences with attractive flower bracts and excellent post-production longevity.

The new Poinsettia plant originated from a cross-pollination made by the Inventor in December, 2007 of a proprietary selection of *Euphorbia pulcherrima* Willd. identified as code number PX 14002, not patented, as the female, or seed, parent, with *Euphorbia pulcherrima* Willd. 'PER2804', disclosed in U.S. Plant Pat. No. 19,295, as the male, or pollen, parent. The new Poinsettia plant was discovered and selected by the Inventor as a single flowering plant from within the progeny of the stated cross-pollination in a controlled greenhouse environment in Encinitas, Calif. in December, 2008.

Asexual reproduction of the new Poinsettia plant by terminal vegetative cuttings in a controlled greenhouse environment in Encinitas, Calif. since February, 2009 has shown that the unique features of this new Poinsettia plant are stable and reproduced true to type in successive generations of asexual reproduction.

SUMMARY OF THE INVENTION

Plants of the new Poinsettia have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'PER1360'. These characteristics in combination distinguish 'PER1360' as a new and distinct Poinsettia plant:

1. Uniform, upright and mounded plant habit.
2. Vigorous growth habit.
3. Freely and upright branching habit.
4. Dark green-colored leaves.
5. Under natural season conditions, plants flower on or about November 10 in Southern California.
6. Large inflorescences with medium red-colored flower bracts.
7. Good post-production longevity.

In side-by-side comparisons conducted in Encinitas, Calif., plants of the new Poinsettia differ primarily from plants of the female parent selection in flower bract color as plants of the female parent selection have darker red-colored flower bracts than plants of the new Poinsettia. In addition, plants of the female parent selection flower about four days earlier than plants of the new Poinsettia.

In side-by-side comparisons conducted in Encinitas, Calif., plants of the new Poinsettia differ primarily from plants of the male parent, 'PER2804', in leaf and flower bract color as plants of 'PER2804' have lighter green-colored leaves and brighter red-colored flower bracts than plants of the new Poinsettia. In addition, plants of 'PER2804' flower about eight days earlier than plants of the new Poinsettia.

Plants of the new Poinsettia can be compared to plants of the *Euphorbia pulcherrima* Willd. 'Peterstar', disclosed in U.S. Plant Pat. No. 8,259. In side-by-side comparisons conducted in Encinitas, Calif., plants of the new Poinsettia differed primarily from plants of 'Peterstar' in the following characteristics:

1. Plants of the new Poinsettia were more vigorous than plants of 'Peterstar'.
2. Plants of the new Poinsettia had a more upright branching habit than plants of 'Peterstar'.
3. Plants of the new Poinsettia had darker green-colored leaves than plants of 'Peterstar'.
4. Plants of the new Poinsettia flowered about 15 days earlier than plants of 'Peterstar'.
5. Plants of the new Poinsettia and 'Peterstar' differed in flower bract color as plants of 'Peterstar' had bright red-colored flower bracts.

Plants of the new Poinsettia can be compared to plants of the *Euphorbia pulcherrima* Willd. '490', disclosed in U.S. Plant Pat. No. 7,825. In side-by-side comparisons conducted in Encinitas, Calif., plants of the new Poinsettia differed primarily from plants of '490' in the following characteristics:

1. Plants of the new Poinsettia were more vigorous than plants of '490'.
2. Plants of the new Poinsettia had a more upright branching habit than plants of '490'.
3. Plants of the new Poinsettia flowered about eight days earlier than plants of '490'.
4. Plants of the new Poinsettia and '490' differed in flower bract color as plants of '490' had dark red-colored flower bracts.

BRIEF DESCRIPTION OF THE PHOTOGRAPHS

The accompanying photographs illustrate the overall appearance of the new Poinsettia plant showing the colors as true as it is reasonably possible to obtain in colored reproductions of this type. Colors in the photographs may differ slightly from the color values cited in the detailed botanical description which accurately describe the colors of the new Poinsettia plant.

The photograph on the first sheet is a side perspective view of a typical flowering plant of 'PER1360' grown in a container.

The photograph on the second sheet is a close-up view of a typical flowering plant of 'PER1360'.

DETAILED BOTANICAL DESCRIPTION

Plants used in the aforementioned photographs and in the following detailed description were grown during the late autumn/early winter in 16.5-cm containers in a polyethylene-covered greenhouse in Encinitas, Calif. and under natural season conditions and cultural practices typical of commercial Poinsettia production. During the production of the plants, day temperatures averaged 26° C., night temperatures averaged 18° C. and light levels averaged 5,000 foot-candles. Measurements and numerical values represent averages for typical flowering plants. Plants were pinched one time and were 21 weeks old when the photographs and the description were taken. In the following description, color references are made to The Royal Horticultural Society Colour Chart, 2007 Edition, except where general terms of ordinary dictionary significance are used.

Botanical classification: *Euphorbia pulcherrima* Willd. 'PER1360'.

Parentage:

*Female, or seed, parent.*—Proprietary selection of *Euphorbia pulcherrima* Willd. identified as code number PX 14002, not patented.

*Male, or pollen, parent.*—*Euphorbia pulcherrima* Willd. 'PER2804', disclosed in U.S. Plant Pat. No. 19,295.

Propagation:

*Type.*—Terminal vegetative cuttings.

*Time to initiate roots.*—About seven to ten days at night temperatures about 20° C. and day temperatures about 27° C.

*Time to produce a rooted young plant.*—About four weeks at night temperatures about 20° C. and day temperatures about 27° C.

*Root description.*—Fibrous; white in color.

Plant description:

*Plant habit and form.*—Uniform, upright and mounded plant habit; inverted triangle; large inflorescences positioned above the foliar plane; vigorous growth habit.

*Plant height.*—About 42 cm.

*Plant diameter or spread.*—About 57.5 cm.

*Lateral branch description.*—Quantity: Freely branching habit, about eight lateral branches develop after pinching; upright branching habit. Length: About 38 cm. Diameter: Thick, about 9 mm. Internode length: About 1.7 cm. Strength: Strong. Aspect: About 30° from vertical. Texture: Smooth, glabrous. Luster: Glossy. Color: More green than 146A.

*Leaf description.*—Arrangement: Alternate, simple. Length: About 12.5 cm. Width: About 10 cm. Shape: Ovate, occasionally with broad lobes. Apex: Acuminate. Base: Mostly truncate, occasionally with cordate tendencies. Margin: Mostly entire, occasionally with broad lobes. Aspect: Flat. Venation pattern: Pinnate, arcuate. Texture, upper and lower surfaces: Smooth, glabrous; slightly rugose. Color: Developing and fully expanded leaves, upper surface: Darker green than N137A or 147A; venation, close to 146A. Developing and fully expanded leaves, lower surface: Close to N137B to N137C; midvein, close to 146B and lateral veins, close to 146B to 146C tinged with close to 187A. Petioles: Length: About 6.8 cm. Diameter: About 4 mm. Texture, upper and lower surfaces: Smooth, glabrous. Luster, upper and lower surfaces: Glossy. Color, upper and lower surfaces: Close to 187A to 187B.

Inflorescence description:

*Inflorescence type and habit.*—Terminal inflorescences are compound corymbs of cyathia with colored flower bracts subtending the cyathia; inflorescences uniformly positioned above the foliar plane.

*Fragrance.*—None detected.

*Flowering response.*—Under natural season conditions, plants typically flower on or about November 10 in Southern California; under artificial long nyctoperiod/short photoperiod conditions, plants flower about seven to eight weeks later.

*Post-production longevity*.—Good post-production longevity; plants of the new Poinsettia maintain good substance and flower bract color for about four to six weeks under interior conditions; flower bracts persistent and cyathia not persistent.

*Inflorescence diameter*.—About 33.5 cm.

*Inflorescence height* (*depth*).—About 4.5 cm.

*Flower bracts*.—Quantity per inflorescence: About 24. Length, largest bracts: About 15.5 cm. Width, largest bracts: About 12 cm. Shape: Ovate; occasionally with broad lobes. Apex: Acuminate. Base: Truncate. Margin: Entire, occasionally with broad lobes and occasionally with serrations. Texture, upper and lower surfaces: Smooth, glabrous; velvety; mostly flat to slightly rugose. Aspect: Mostly horizontal; older bracts, drooping. Venation pattern: Pinnate, arcuate. Color: Developing or transitional bracts, upper surface: Ground color, darker green than N137A or 147A; irregular and random sectors, close to brighter and more intense red than 45B. Developing or transitional bracts, lower surface: Ground color, close to 146A; irregular and random sectors, close to 45A. Fully expanded bracts, upper surface: Close to 45B; color does not fade with development. Fully expanded bracts, lower surface: Duller red than 45B; color does not fade with development. Bract petioles: Length: About 3.5 cm. Diameter: About 3.25 mm. Texture, upper and lower surfaces: Smooth, glabrous. Color, upper surface: Close to 187B. Color, lower surface: Close to 146A.

*Cyathia*.—Quantity per corymb: About 15. Length: About 8 mm. Width: About 7 mm. Shape: Oval. Texture: Smooth, glabrous. Color, inner surface: Close to 144A. Color, outer surface: Close to 144A; towards the apex, close to 53A.

*Nectaries*.—Quantity per cyathium: One. Length: About 7 mm. Width: About 4 mm. Shape: Roughly oval. Texture: Smooth, glabrous. Color, inner and outer surfaces: Close to 17A.

*Peduncles*.—Length: About 8 mm. Diameter: About 2.5 mm. Strength: Strong. Aspect: Mostly upright. Texture: Smooth, glabrous. Color: Close to 146A.

*Reproductive organs*.—Stamens: Quantity per cyathium: About 20. Filament length: About 5 mm. Filament color: Close to 154D. Anther shape: Round; bi-lobed. Anther length: Less than 1 mm. Anther color: Close to 9A. Amount of pollen: None observed. Pistils: Pistil development has not been observed on plants of the new Poinsettia.

*Seeds and fruits*.—Seed and fruit production have not been observed on plants of the new Poinsettia.

Disease & pest resistance: Plants of the new Poinsettia have not been shown to be resistant to pathogens and pests common to Poinsettia plants.

Temperature tolerance: Plants of the new Poinsettia have been observed to tolerate temperatures ranging from about 16° C. to about 29° C.

It is claimed:

1. A new and distinct Poinsettia plant named 'PER1360' as illustrated and described.

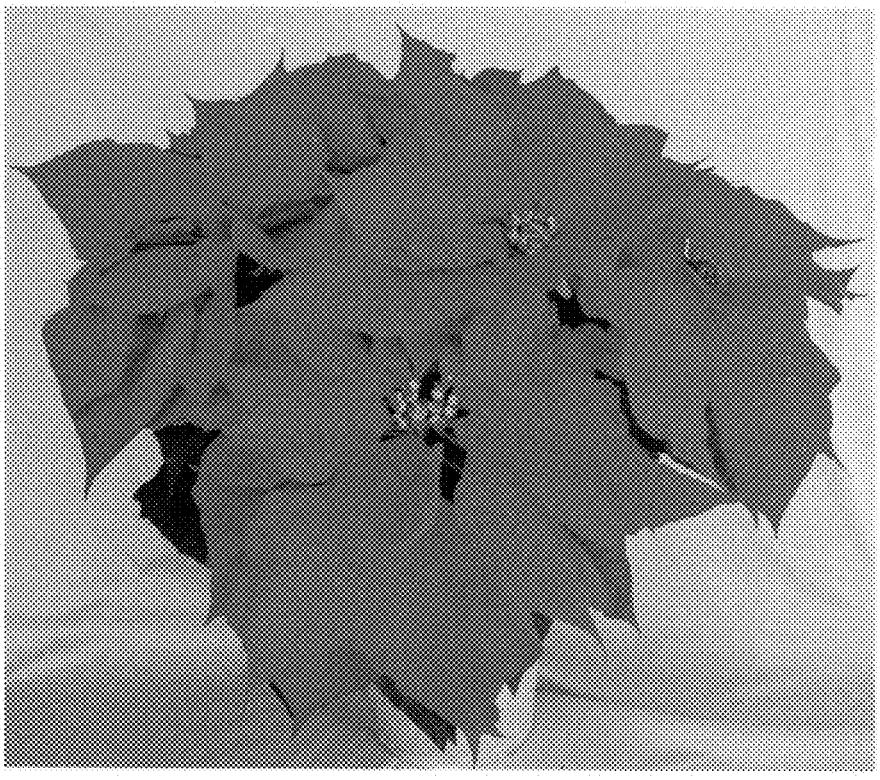

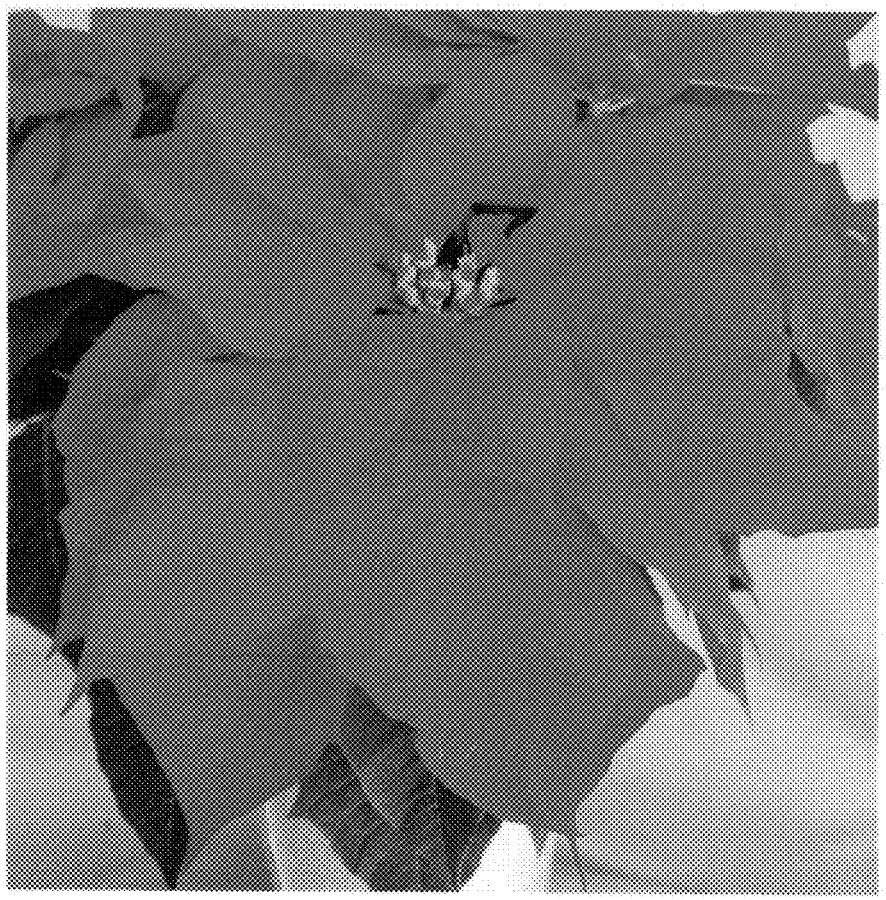

* * * * *